(12) United States Patent
Noguchi et al.

(10) Patent No.: US 11,419,555 B2
(45) Date of Patent: Aug. 23, 2022

(54) IMAGE CAPTURING APPARATUS AND METHOD

(71) Applicant: Hitachi, Ltd., Tokyo (JP)

(72) Inventors: Yoshimi Noguchi, Tokyo (JP); Masahiro Ogino, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 1357 days.

(21) Appl. No.: 15/304,072

(22) PCT Filed: Feb. 5, 2015

(86) PCT No.: PCT/JP2015/053306
§ 371 (c)(1),
(2) Date: Oct. 14, 2016

(87) PCT Pub. No.: WO2015/162968
PCT Pub. Date: Oct. 29, 2015

(65) Prior Publication Data
US 2017/0035364 A1 Feb. 9, 2017

(30) Foreign Application Priority Data

Apr. 21, 2014 (JP) .............................. JP2014-087428

(51) Int. Cl.
*A61B 5/00* (2006.01)
*A61B 5/055* (2006.01)
(Continued)

(52) U.S. Cl.
CPC ............ *A61B 5/7203* (2013.01); *A61B 5/055* (2013.01); *A61B 5/7253* (2013.01); *A61B 6/027* (2013.01);
(Continued)

(58) Field of Classification Search
CPC ...... A61B 5/7203; A61B 5/055; A61B 5/7253
See application file for complete search history.

(56) References Cited

U.S. PATENT DOCUMENTS 6,524,253 B1 2/2003 Abend
7,592,808 B1 * 9/2009 King ................ G01R 33/56545
324/307

(Continued)

FOREIGN PATENT DOCUMENTS

CN 101975936 A 2/2011
CN 102947864 A 2/2013
(Continued)

OTHER PUBLICATIONS

Japanese-language Office Action issued in counterpart Japanese Application No. 2016-254839 dated Jan. 9, 2018 with English translation (Five (5) pages).
(Continued)

*Primary Examiner* — Joseph M Santos Rodriguez
(74) *Attorney, Agent, or Firm* — Crowell & Moring LLP

(57) ABSTRACT

To acquire a higher-quality image with high-speed imaging in an MRI apparatus or the like to which compressed sensing is applied. Included are: an observation unit that does not observe, when any one of two points being point-symmetric with respect to the origin is observed, the other point in observation of a high frequency component of a K-space of the MRI apparatus; and a reconstruction unit that reconstructs an image from a component of the K-space observed by the observation unit. The reconstruction process of the reconstruction unit includes an image correction process based on an observation pattern of the observation unit.

9 Claims, 7 Drawing Sheets

(51) Int. Cl.
  *G01R 33/56* (2006.01)
  *A61B 6/02* (2006.01)
  *G01R 33/561* (2006.01)
  *A61B 6/00* (2006.01)
  *A61B 6/03* (2006.01)
  *A61B 8/14* (2006.01)
  *G06T 5/00* (2006.01)
  *G06T 11/00* (2006.01)
  *A61B 8/00* (2006.01)
  *G01R 33/48* (2006.01)

(52) U.S. Cl.
  CPC ............ *A61B 6/032* (2013.01); *A61B 6/5205* (2013.01); *A61B 8/14* (2013.01); *G01R 33/56* (2013.01); *G01R 33/561* (2013.01); *G01R 33/5608* (2013.01); *G06T 5/002* (2013.01); *G06T 11/003* (2013.01); *A61B 8/00* (2013.01); *A61B 2576/00* (2013.01); *G01R 33/482* (2013.01); *G01R 33/4824* (2013.01); *G06T 2207/10088* (2013.01)

(56) References Cited

U.S. PATENT DOCUMENTS

| | | | |
|---|---|---|---|
| 9,702,953 B1* | 7/2017 | Xiao .................... | G01R 33/561 |
| 2002/0022780 A1 | 2/2002 | Kawagishi et al. | |
| 2004/0122316 A1 | 6/2004 | Satoh | |
| 2008/0219535 A1 | 9/2008 | Mistretta et al. | |
| 2011/0095762 A1* | 4/2011 | Piccini ............... | G01R 33/4824 324/312 |
| 2011/0144497 A1 | 6/2011 | Kim | |
| 2012/0265050 A1 | 10/2012 | Wang | |
| 2013/0083886 A1 | 4/2013 | Carmi et al. | |
| 2014/0152303 A1* | 6/2014 | Wang .................. | G01R 33/561 324/309 |
| 2016/0370444 A1 | 12/2016 | Peng et al. | |

FOREIGN PATENT DOCUMENTS

| | | |
|---|---|---|
| CN | 103163496 A | 6/2013 |
| CN | 103654789 A | 3/2014 |
| CN | 103679654 A | 3/2014 |
| JP | 2000-279391 A | 10/2000 |
| JP | 2000-325344 A | 11/2000 |
| JP | 2001-269336 A | 10/2001 |
| JP | 2001-327505 A | 11/2001 |
| JP | 2002-224101 A | 8/2002 |
| JP | 2003-501195 A | 1/2003 |
| JP | 2004-174226 A | 6/2004 |
| JP | 2008-200478 A | 9/2008 |
| JP | 2011-120869 A | 6/2011 |
| JP | 2013-529491 A | 7/2013 |

OTHER PUBLICATIONS

Chinese Office Action issued in counterpart Chinese Application No. 201580020620.4 dated Aug. 29, 2018 (eight (8) pages).
International Search Report (PCT/ISA/210) issued in PCT Application No. PCT/JP2015/053306 dated Apr. 28, 2015 with English translation (Four (4) pages).
Japanese-language Written Opinion (PCT/ISA/237) issued in PCT Application No. PCT/JP2015/053306 dated Apr. 28, 2015 (Five (5) pages).
Lustig, M., et al., "Sparse MRI: The Application of Compressed Sensing for Rapid MR Imaging", Magnetic Resonance in Medicine, 2007, vol. 58, pp. 1182-1195 (Fourteen (14) pages).
Plonka, G., et al., "Curvelet-Wavelet Regularized Split Bregman Iteration for Compressed Sensing", International Journal of Wavelets, Multiresolution and Information Processing, 2011, pp. 1-28 (Twenty-eight (28) pages).

* cited by examiner

Moving average values    Gaussian filter values

IMAGE CAPTURING APPARATUS AND METHOD

TECHNICAL FIELD

The present invention relates to a magnetic resonance imaging apparatus or the like, and particularly to a high-speed and high-quality image capturing technology.

BACKGROUND ART

Magnetic resonance imaging (MRI) is a method of imaging in-vivo information using a nuclear magnetic resonance (NMR) phenomenon and is similar to computed tomography (CT) in terms of obtaining a tomographic image, but can visualize physical information, which is not obtained by the CT. In addition, there is no exposure to radiation. However, there is a problem that time for inspection is long upon its nature. In general, the MRI requires several tens of minutes for each subject, and a patient receives a lot of loads such as needs to stop respiration for several tens of seconds in order to photograph or image the abdomen or lung so that there is a demand for an increase in speed of imaging. High-speed imaging called parallel imaging has been used as such a method, but has problems that image quality deteriorates and noise increases as an increasing rate of speed becomes high.

Recently, studies have been conducted regarding application of a method called compressed sensing (CS) to an MRI apparatus (NPL 1). The CS uses sparsity of a signal, and can restore an original signal from a result of sparse observation with high accuracy. Herein, the sparse observation indicates that observation is performed for the amount of data smaller than the amount of data to be reconstructed. To use what kind of observation pattern is an important point in the compressed sensing. In general, a random binary matrix, a weighted random matrix, a radial-line form, a spiral form, a parallel-line form, or the like is frequently used.

CITATION LIST

Patent Literature

NPL 1: Lustig et al., "Sparse MRI: The Application of Compressed Sensing for Rapid MR Imaging," Magnetic Resonance in Medicine, 58 1182-1195, 2007

NPL 2: G. Plonka, J. Ma, Curvelet-Wavelet Regularized Split Bregman Iteration for Compressed Sensing, International Journal of Wavelets, Multiresolution and Information Processing, 1-28, 2011

SUMMARY OF INVENTION

Technical Problem

In regard to the observation pattern of the CS described above, a signal collection orbit can be selected in random (two-dimensionally) in the case of performing three-dimensional imaging in the MRI apparatus, for example, but there are many unclear points on a relation with the image quality, and there is no clear rule. In addition, the orbit is changed only in a phase encoding direction (one-dimensionally) in the case of two-dimensional imaging, and thus, a parallel-line form observation pattern, for example, becomes a prerequisite, and there is a problem in relation to a compression rate or restoration performance. In addition, the image quality of an image restored by the CS is greatly affected by parameters at the time of reconstruction, but it is extremely difficult to suitably control values of those parameters.

An object of the present invention is to provide an image capturing apparatus and method capable of solving the above-described problems.

Solution to Problem

In order to achieve the above-described object, the present invention provides an image capturing apparatus that images an image of a subject, the image capturing apparatus including: an observation unit which performs observation of the subject and outputs observation data; and a reconstruction unit which reconstructs an image from the observation data from the observation unit, in which the observation unit acquires the observation data based on an observation pattern to perform sparse observation, and the reconstruction unit performs an image correction process based on the observation pattern with respect to the observation data.

In addition, in order to achieve the above-described object, the present invention provides an image capturing apparatus that images an image of a subject, the image capturing apparatus including: an observation unit which performs observation of the subject and outputs observation data of a K-space; and a reconstruction unit which reconstructs an image from the observation data from the observation unit, in which the observation unit acquires the observation data of the K-space based on an observation pattern to perform sparse observation, and does not perform observation, when any one between two points which are point-symmetric with respect to an origin of the K-space is observed in observation of a high frequency component of the K-space, for the other point.

Further, in order to achieve the above-described object, the present invention provides an image capturing method that images an image of a subject, the image capturing method including: acquiring observation data of the subject based on an observation pattern to perform sparse observation; and performing an image correction process based on the observation pattern with respect to the observation data when an image is reconstructed from the observation data.

Advantageous Effects of Invention

According to the present invention, it is possible to acquire a high-quality image with high-speed imaging by an image capturing apparatus.

DESCRIPTION OF EMBODIMENTS

Figure 1:
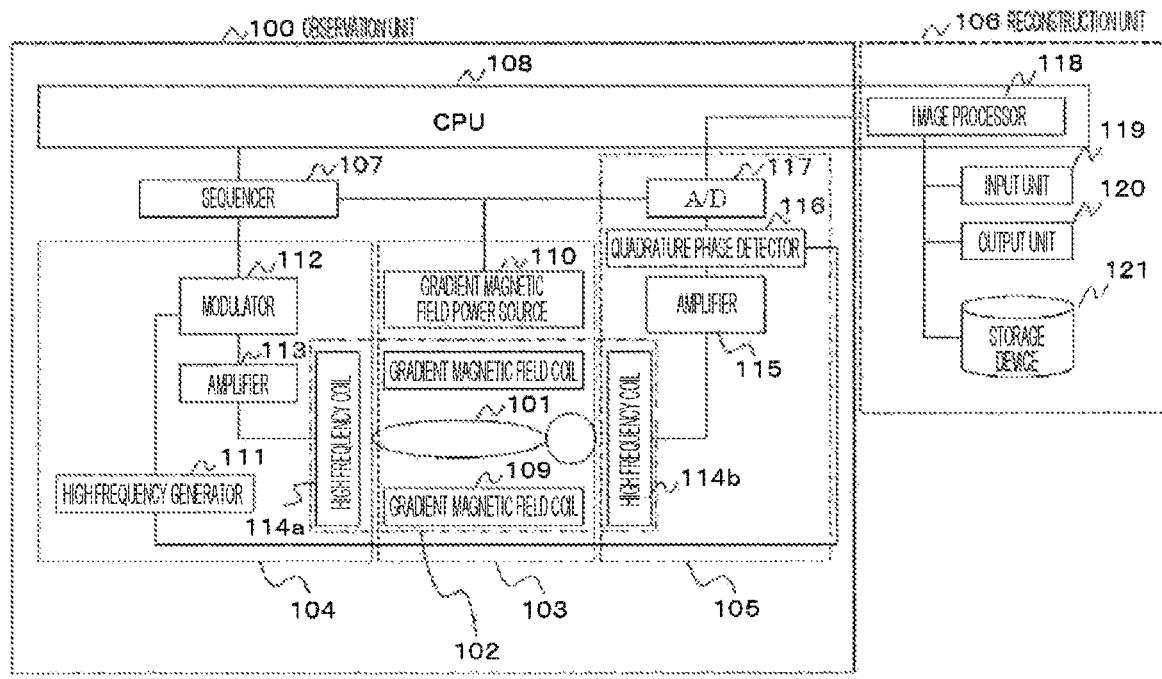
FIG. 1 is a block diagram illustrating an example of the entire configuration of an MRI apparatus according to Embodiments 1 to 3.

Hereinafter, embodiments of an image capturing apparatus of the present invention will be described in accordance with the drawings, and first, a description will be given regarding a configuration example of an MRI apparatus, which is a kind of the image capturing apparatus, to be commonly used in Embodiments 1 to 3 with reference to FIG. 1. As apparent from FIG. 1, the MRI apparatus is configured of an observation unit 100 which observes a subject and a reconstruction unit 106 which reconstructs an image of the observed subject when roughly divided.

The observation unit 100 is configured of a static magnetic field generation system 102, a gradient magnetic field generation system 103, a transmission system 104, a reception system 105, a sequencer 107, and a central processing unit (CPU) 108. The static magnetic field generation system 102 generates a uniform magnetic field in a space surrounding a subject 101. A permanent magnet or a magnetic field generating means such as a normal conducting system or a superconducting system is arranged. The gradient magnetic field generation system 103 is configured of a gradient magnetic field coil 109 and a gradient magnetic field power source 110 that drives the gradient magnetic field coil 109, and applies a gradient magnetic field to the subject 101.

The sequencer 107 is a control mean that repeatedly applies a high frequency magnetic field pulse (RF pulse) and a gradient magnetic field pulse with a predetermined pulse sequence, operates under control of the CPU 108, and transmits various commands, required for data collection of a tomographic image of the subject 101 to the transmission system 104, the gradient magnetic field generation system 103, and the reception system 105. The transmission system 104 is configured of a high frequency generator 111, a modulator 112, an amplifier 113, and a high frequency coil 114a, and emits an RF pulse which causes nuclear magnetic resonance with a nuclear spin of an atom forming the subject 101. The reception system 105 is configured of a high frequency coil 114b, an amplifier 115, a quadrature phase detector 116, and an A/D converter 117, receives an echo signal, which is released from the nuclear magnetic resonance of the nuclear spin, and transmits the echo signal to the reconstruction unit 106.

The reconstruction unit 106 is configured of an image processor 118, an input unit 119 including a keyboard, a mouse, a touch panel, a button and the like, an output unit 120 including a display, a printer and the like, and a storage apparatus 121 including a magnetic disk, an optical disk and the like and storing data and a desired program. The image processor 118 reconstructs an image when data is input from the reception system 105, displays the image using the output unit 120, and records the image in the storage apparatus 121. As illustrated in FIG. 1, the image processor 118 can be implemented by program processing using the CPU 108, but it is also possible to install another central processing unit (CPU), different from the CPU 108, in the reconstruction unit 106, or to configure the image processor 118 using a dedicated hardware for image processing.

Figure 2:
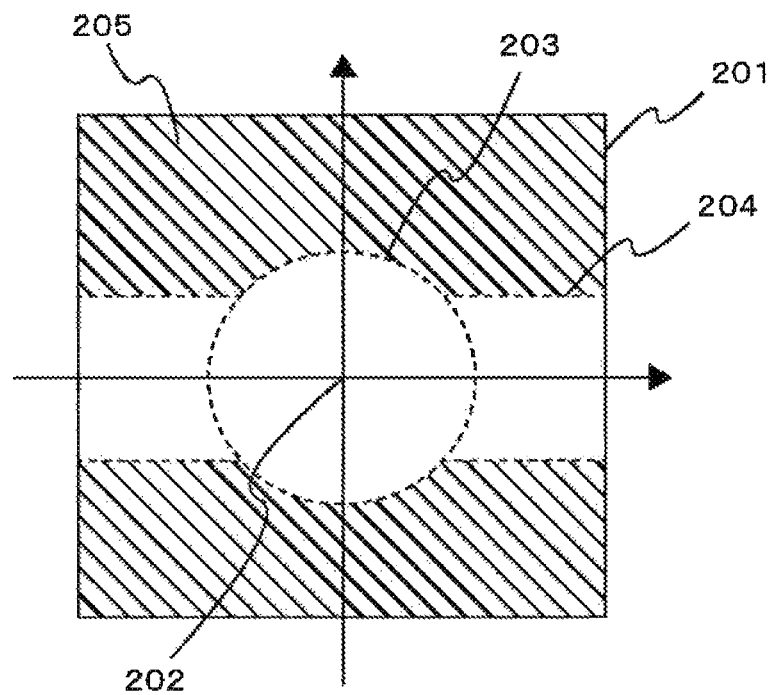
FIG. 2 is a diagram for describing an observation method of the MRI apparatus according to Embodiment 1.
Figure 3:
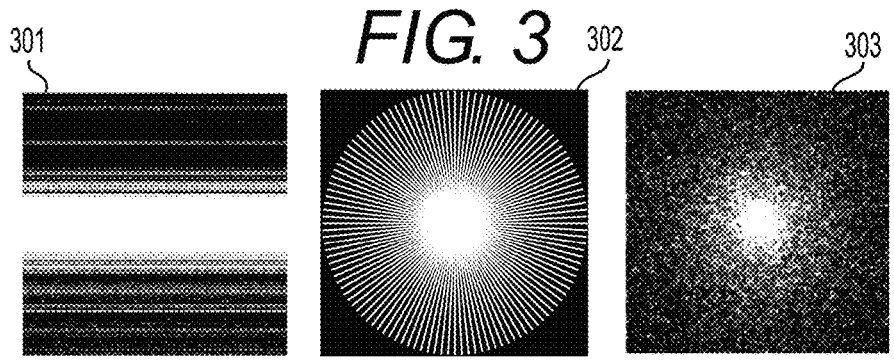
FIG. 3 is a diagram illustrating an example of an observation pattern of the MRI apparatus according to Embodiment 1.

Next, a description will be given regarding an observation method of the echo signal, which is received by the reception system 105 in the observation unit 100 of the MRI apparatus of FIG. 1, that is, K-space data with reference to FIG. 2. In FIG. 2, 201 represents a K-space serving as an observation target (space obtained by a Fourier transform of image data of a real space), 202 represents an origin of the K-space 201, 203 represents a low frequency component region near the origin, 204 represents a low frequency component region near an axis thereof, and 205 represents a high frequency component region. It is necessary to reduce data points to be observed in order for high-speed imaging. In general, it is considered that it is preferable to observe a space serving as an observation target in random in CS. This is for observation of a signal component without any deviation. However, a significant change is generated in contrast or brightness of a reconstructed image in the K-space unless the low frequency component region 203 or 204 near the origin is closely observed, and thus, the entire element is observed in relation to the low frequency component 203 or 204 near the origin. A parallel-line form 301, a radial form 302, and a random form 303, which are illustrated in FIG. 3, and further, a spiral form (not illustrated) are considered as the observation pattern according to the above-described observation method.

Figure 4:
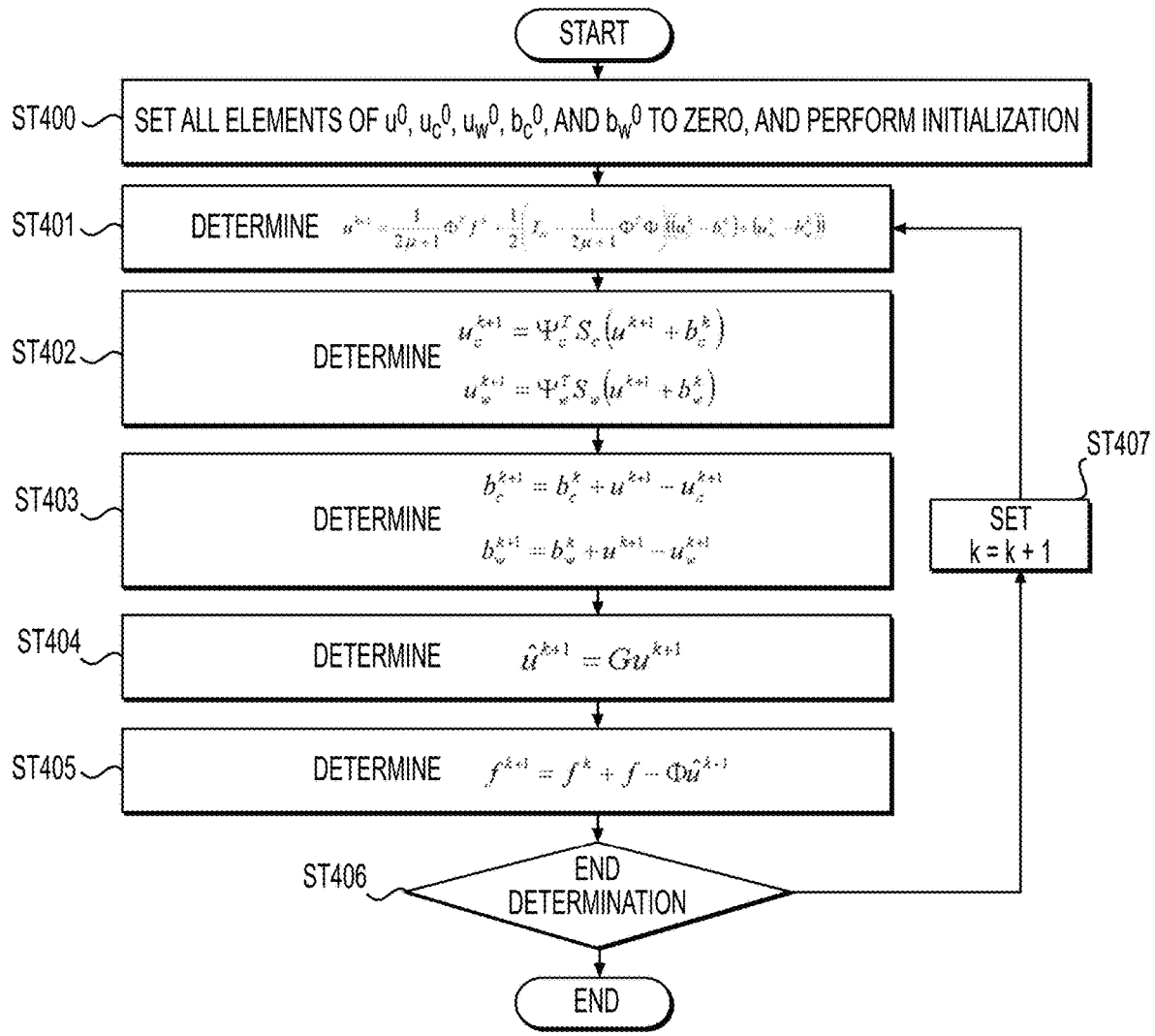
FIG. 4 is a diagram illustrating a reconstruction process flow of the MRI apparatus according to Embodiment 1.

Next, a description will be given regarding processing content of the image processor 118 of the MRI apparatus of FIG. 1. As described above, the image processor 118 is implemented by the program processing preferably using the CPU. FIG. 4 illustrates a process flow that is implemented by the program processing or the like of the image processor 118. When the observation pattern that has been described with reference to FIG. 3 is used, artifacts such as a false edge and a blur are generated as compared to the case of observing the entire element. Thus, the image processor 118 reconstructs a sharp image without any artifact while solving a problem of minimizing cost. Any solution may be employed as a solution to the minimization problem, and a description will be given in the following embodiments regarding a cost minimizing method which employs a Split Bregman method (NPL 2).

Embodiment 1

Embodiment 1 is an embodiment of an MRI apparatus which is an image capturing apparatus that images an image of a subject. The image capturing apparatus includes the observation unit 100, which performs observation of the subject and outputs observation data, and the reconstruction unit 106 which reconstructs an image from the observation data from the observation unit. The observation unit 100 acquires the observation data based on an observation pattern to perform sparse observation. The reconstruction unit 106 performs an image correction process based on the observation pattern with respect to the observation data.

As illustrated in FIG. 4, the image processor 118 of the present embodiment reconstructs the image from an observed K-space by repeatedly executing step ST401 to step ST407. Although the cost minimization and sequential optimization are performed using the Split Bregman method in the image processor 118 as described above, the present embodiment uses a result corrected by an image correction process in an estimation updating process thereof.

First, all elements of $u^0$, $u_c^0$, $u_w^0$, $b_c^0$ and $b_w^0$ are initialized to zero in step ST400 as illustrated in FIG. 4. Thereafter, step ST401 to step ST407 are repeatedly executed.

Hereinafter, a (k+1)-th repeat will be described. Formula (1) is calculated in step ST401, and an estimation result $u^{k+1}$ is calculated.

[Formula 1]

$$u^{k+1} = \frac{1}{2\mu+1}\Phi^T f^k + \frac{1}{2}\left(I_N - \frac{1}{2\mu+1}\Phi^T\Phi\right)((u_c^k - b_c^k) + (u_w^k - b_w^k)) \quad (1)$$

Herein, $f^k$ represents a K-space updated by an immediately previous (k-th) repeat, $\Phi$ represents an observation process using the Fourier transform and the observation pattern, and $\Phi^T$ represents an inverse transform of $\Phi$. IN represents an array whose entire element is one and which has the same size as $f^k$. In addition, $u_c^k$, $u_w^k$, $b_c^k$, and $b_w^k$ are changing components which are calculated in the immediately previous (k-th) repeat. In addition, p represents a positive constant as a parameter.

Next, $u_c^{k+1}$ and $u_w^{k+1}$ are calculated from Formulas (2) and (3) in step ST402.

[Formula 2]

$$u_c^{k+1} = \Psi_c^T S_c(u^{k+1} + b_c^k) \quad (2)$$

[Formula 3]

$$u_w^{k+1} = \Psi_w^T S_w(u^{k+1} + b_w^k) \quad (3)$$

Herein, $\Psi_c^T$ and $\Psi_w^T$ represent a curvelet inverse transform and a wavelet inverse transform, respectively. Although the curvelet transform and the wavelet transform are used herein, in addition to these, a TV (total variation), a ridgelet transform, and the like may be used. In addition, they may be combinedly used.

$S_c$ and $S_w$ represent a process called soft shrinkage. $S_c$ and $S_w$ perform the processes shown in Formulas (4) and (5), respectively, with respect to the entire element. Herein, $\Psi_c$ and $\Psi_w$ represent a curvelet transform and a wavelet transform, respectively. In addition, $\lambda$ is a constant as a parameter.

[Formula 4]

$$S_c(u^{k+1} + b_c^k) = \begin{cases} \Psi_c(u^{k+1} + b_c^k) - \frac{|\lambda|}{\mu} & \text{if } \Psi_c(u^{k+1} + b_c^k) \geq \frac{|\lambda|}{\mu} \\ \Psi_c(u^{k+1} + b_c^k) + \frac{|\lambda|}{\mu} & \text{if } \Psi_c(u^{k+1} + b_c^k) \leq \frac{|\lambda|}{\mu} \\ 0 & \text{if}|\Psi_c(u^{k+1} + b_c^k)| < \frac{|\lambda|}{\mu} \end{cases} \quad (4)$$

[Formula 5]

$$S_w(u^{k+1} + b_w^k) = \begin{cases} \Psi_w(u^{k+1} + b_w^k) - \frac{|\lambda|}{\mu} & \text{if } \Psi_w(u^{k+1} + b_w^k) \geq \frac{|\lambda|}{\mu} \\ \Psi_w(u^{k+1} + b_w^k) + \frac{|\lambda|}{\mu} & \text{if } \Psi_w(u^{k+1} + b_w^k) \leq \frac{|\lambda|}{\mu} \\ 0 & \text{if}|\Psi_w(u^{k+1} + b_w^k)| < \frac{|\lambda|}{\mu} \end{cases} \quad (5)$$

Next, $b_c^{k=1}$ and $b_w^{k+1}$ are calculated using Formulas (6) and (7) in step ST403.

[Formula 6]

$$b_c^{k+1} = b_c^k + u^{k+1} - u_c^{k+1} \quad (6)$$

[Formula 7]

$$b_w^{k+1} = b_w^k + u^{k+1} - u_w^{k+1} \quad (7)$$

In step ST404, a correction process G, based on the observation pattern in the present embodiment as described above, is performed with respect to the estimation result $u^{k+1}$ as shown in Formula (8). That is, a result corrected through the correction process G is used in the estimation updating process. Accordingly, the MRI apparatus of the present embodiment is capable of improving the image quality of the image to be reconstructed.

[Formula 8]

$$\hat{u}^{k+1} = Gu^{k+1} \quad (8)$$

Here, a description will be given regarding the correction process G based on the observation pattern 301 in the case of using the horizontally parallel-line form observation pattern 301 illustrated in FIG. 3 as the observation method according to the observation unit 100 of the present embodiment with reference to FIG. 5.

Figure 5:
FIG. 5 is a diagram for describing a correction process based on the observation pattern of the MRI apparatus according to Embodiment 1.
Figure 5:
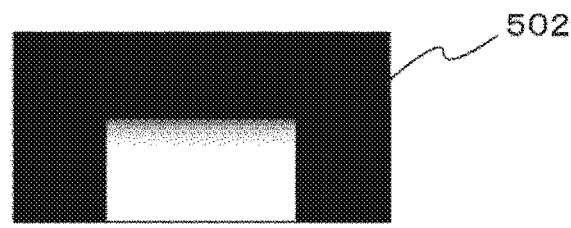

In FIG. 5, 501 represents a true horizontal edge image that is desirably reconstructed, and 502 represents an image of a reconstructed image obtained by the reconstruction unit 106 in the case of using the parallel-line form observation pattern 301 illustrated in FIG. 3. As apparent from the image 502 of the same drawing, a horizontal edge blurs and is likely to be reconstructed. This is because a high frequency component corresponding to the horizontal edge is hardly acquired in the observation using the parallel-line form observation pattern 301 illustrated in FIG. 3.

Thus, a horizontal edge smoothing process is used based on the observation pattern 301 as the correction process G according to the above-described Formula (8) in the present embodiment in order to further sharpen the horizontal edge of the reconstructed image. In addition, the reconstruction is performed using a reconstruction algorithm that makes an estimation result obtained after smoothing approximate to the input observation data. Accordingly, it is possible to estimate a sharper horizontal edge.

Figure 6:
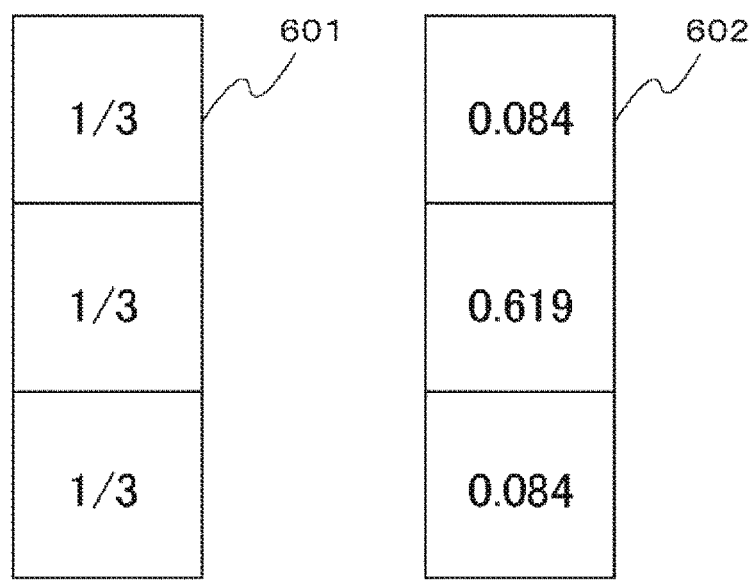
FIG. 6 is an example of a horizontal edge smoothing filter of the MRI apparatus according to Embodiment 1.

Incidentally, any process may be performed as the above-described horizontal edge smoothing process. For example, a one-dimensional moving average filter 601 or a one-dimensional Gaussian filter 602 are considered as illustrated in FIG. 6.

In addition, a blur in a certain direction is not generated in the case of using the radial observation pattern 302 or the random form observation pattern 303 illustrated in FIG. 3 instead of the parallel-line form observation pattern 301, and thus, it is considered to apply a two-dimensional Gaussian filter, for example, as the smoothing process.

Figure 7:
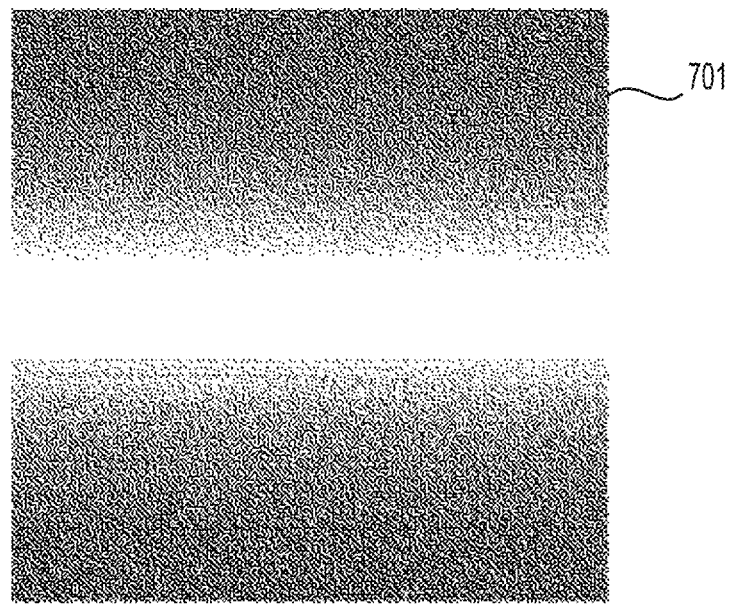
FIG. 7 is a diagram that smoothes a parallel-line form observation pattern of the MRI apparatus according to Embodiment 1.

In addition, a sufficiently smoothed observation pattern may be used as illustrated in FIG. 7. In the same drawing, 701 represents a sufficiently smoothed parallel-line form observation pattern. This may be used as a filter of the correction process G.

Returning to the process flow of FIG. 4, step ST405 is a process of updating $f^{k+1}$ from the estimation result corrected in step ST404 using Formula (9).

[Formula 9]

$$f^{k+1} = f^k + f - \Phi \hat{u}^{k+1} \qquad (9)$$

Finally, end determination is performed in step ST406. Any reference may be used as a reference to be used in the end determination. For example, an absolute value or an average value of $b_c^{k-1}$ and $b_w^{k+1}$ a difference value from the immediately previous repeat, a loop count k, or the like are considered. In addition, the end determination may be performed with respect to the estimation result using a new evaluation index. When the end determination is not satisfied, k is updated in step ST407, and the process returns to step ST401. Incidentally, the update may be performed so as to gradually increase the parameter μ in step ST407. When the end determination is satisfied, $u^{k+1}$ is output as a reconstructed image.

According to Embodiment 1 described above, improvement of a PSNR (peak signal noise ratio) by several dB is expected by causing the correction process based on the observation pattern according to the observation unit to be incorporated in the reconstruction process according to the reconstruction unit. That is, it is possible to acquire a high-quality image using the observation data which is obtained by the observation pattern to perform sparse observation according to the image capturing apparatus of the present embodiment. That is, high-speed imaging is possible by obtaining smaller data using the observation pattern to perform sparse observation, and the reconstruction of the high-quality image is possible by performing the correction process based on the observation pattern. In addition, it is possible to significantly reduce image quality adjusting work of a user.

Embodiment 2

Embodiment 2 is an embodiment of the MRI apparatus which is an image capturing apparatus that images an image of a subject. The image capturing apparatus includes the observation unit 100, which performs observation of the subject and outputs observation data of a K-space, and the reconstruction unit 106 which reconstructs an image from the observation data from the observation unit. The observation unit 100 acquires the observation data of the K-space based on an observation pattern to perform sparse observation, and does not perform observation, when any one between two points which are point-symmetric with respect to the origin of the K-space is observed in observation of a high frequency component of the K-space, for the other point.

The entire configuration of the apparatus is also illustrated in FIG. 1 in the present embodiment similarly to Embodiment 1. A point of the present embodiment different from Embodiment 1 is an observation method of observation data which is an echo signal in the observation unit 100. The reconstruction unit 106 is the same as in Embodiment 1.

Figure 8:
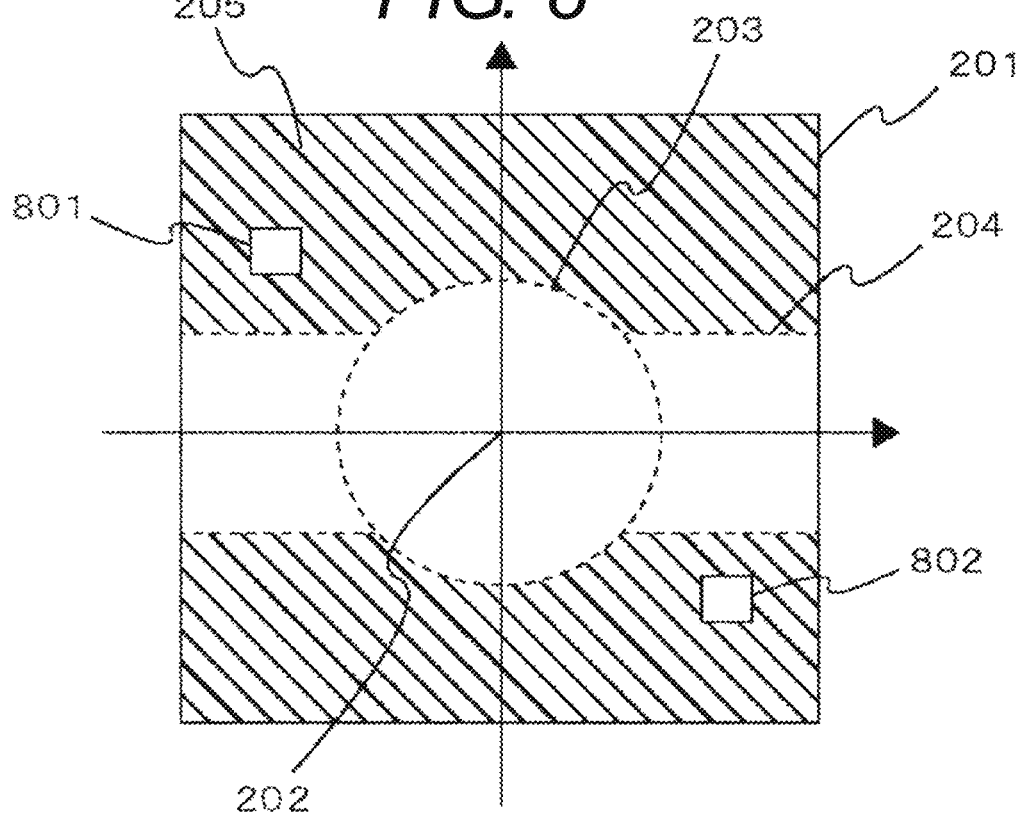
FIG. 8 is a diagram illustrating an observation method of the MRI apparatus according to Embodiment 2.
Figure 9:
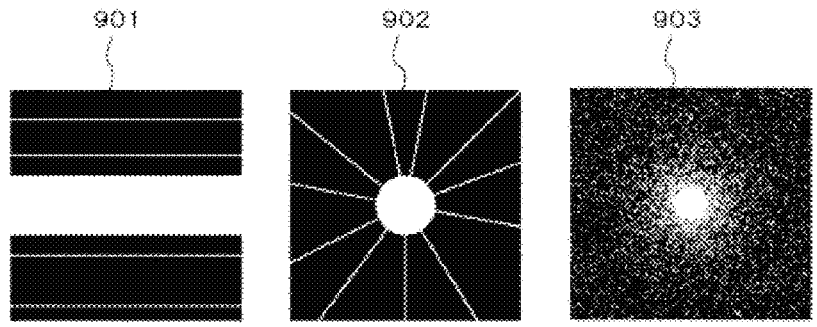
FIG. 9 is a diagram illustrating an example of an observation pattern of the MRI apparatus according to Embodiment 2.

FIG. 8 is a diagram schematically illustrating the observation method of observation data according to the present embodiment. In FIG. 8, the same elements as the constituent elements illustrated in FIG. 2 will be denoted by the same reference signs, and the description thereof will be omitted. In the same drawing, 801 and 802 represent two points at positions which are point-symmetric with respect to the origin 202 of the K-space 201. In the present embodiment, the observation unit 100 of the MRI apparatus of FIG. 1 performs observation using an observation pattern in which, when one point between the point 801 and the point 802, at the positions which are point-symmetric with respect to the origin 202 of the K-space 201 in the high frequency region 205, is observed, the other point is not observed. FIG. 9 illustrates an example of the observation pattern which is used in the above-described observation method of the present embodiment. A parallel-line form observation pattern 901, which is asymmetric with respect to the horizontal axis, a radial observation pattern 902 to perform observation in angular directions that do not overlap each other even when being rotated by 180 degrees, and the like are used in the case of observing a two-dimensional K-space. In addition, a random form the observation pattern 903, that satisfies the above-described condition, can be also used in the case of observing a three-dimensional K-space.

Since the K-space has the point-symmetry, it is possible to efficiently perform observation by employing the above-described observation method of observing only one of the point-symmetric positions. Accordingly, it is possible to expect the improvement in the image quality of the image to be reconstructed in the image processor 118 of the MRI apparatus. In addition, a value may be inserted using the point-symmetry when the observed K-space is input to the reconstruction unit 106.

As above, it is possible to acquire a higher-quality image with high-speed imaging using smaller observation data by the MRI apparatus according to the present embodiment. Incidentally, it is possible to obtain a specific effect of Embodiment 2 that it is possible to efficiently perform observation even when the correction process based on the observation pattern, which has been described in Embodiment 1, is not incorporated in the reconstruction process in the reconstruction unit 106 according to the present embodiment.

Embodiment 3

Embodiment 3 is an embodiment of the MRI apparatus which is an image capturing apparatus, and is configured such that an observation unit that observes an image acquires observation data based on an observation pattern to perform sparse observation, and a reconstruction unit performs image correction processes based on the observation pattern.

Figure 10:
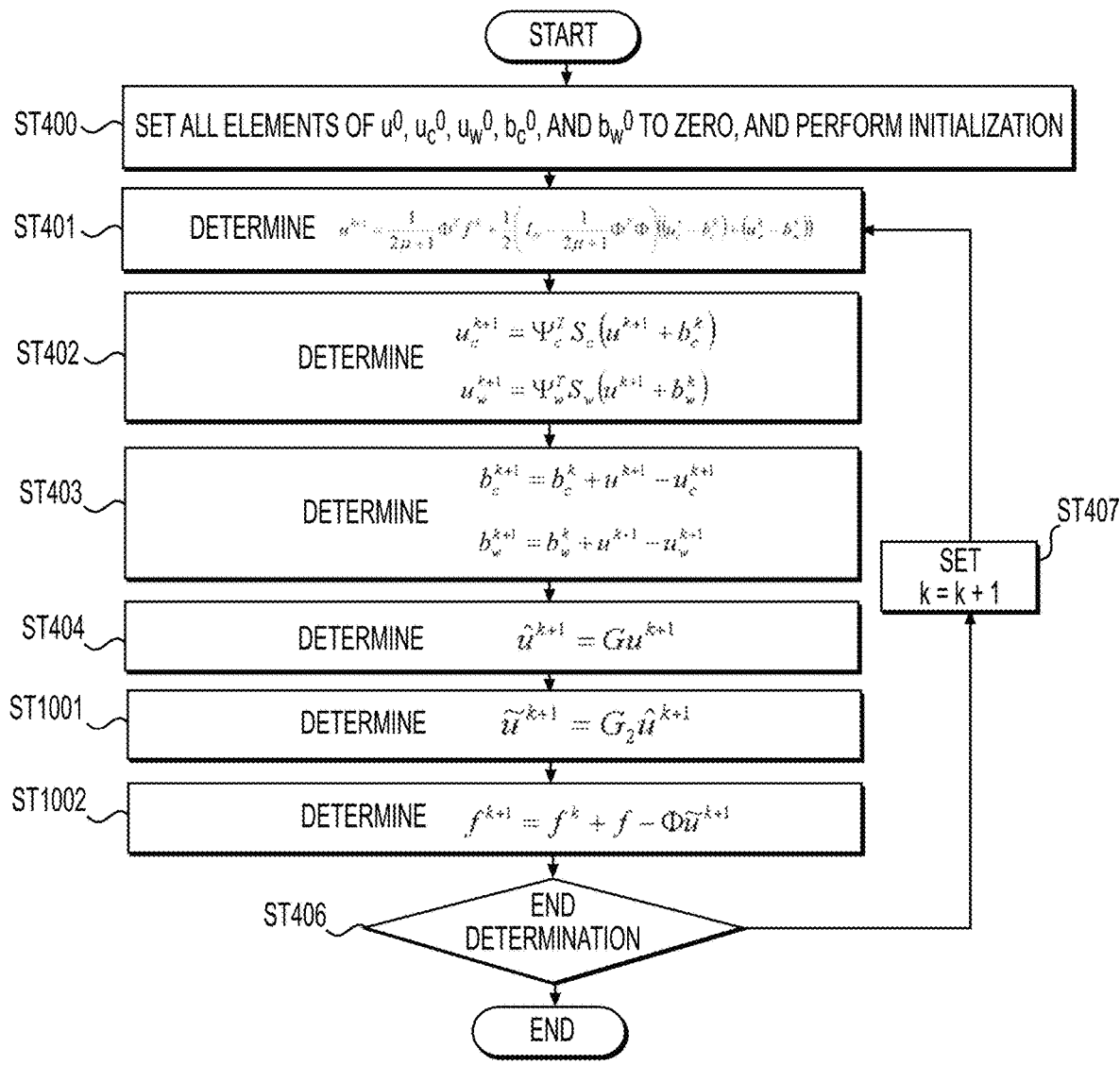
FIG. 10 is a diagram illustrating a reconstruction process flow of the MRI apparatus according to Embodiment 3.

FIG. 10 illustrates a process flow of the image processor 118 according to Embodiment 3. In FIG. 10, the same elements as the constituent elements illustrated in FIG. 4 will be denoted by the same reference signs, and the description thereof will be omitted. In addition, the entire configuration of the apparatus is illustrated in FIG. 1 similarly to Embodiments 1 and 2.

According to the present embodiment, it is possible to more simply adjust image quality of a reconstructed image, and to significantly reduce the image quality adjusting work of the user. A point of the present embodiment different from Embodiment 1 is the configuration in which step ST1001 is newly added in the process flow of the image processor 118 of the reconstruction unit 106, and the correction processes are performed as illustrated in FIG. 10. That is, the plurality of correction processes are prepared and executed.

In general, it is necessary to adjust the variable μ of Formula (1) and the constant λ of Formulas (4) and (5) in order to change the image quality of the reconstructed image, there is low sensitivity in a relationship between these parameters μ and λ, and the reconstructed image, which is different from people's subjectivity. In addition, it is necessary to set these parameters for each imaging target and part, and further, it is difficult for the user to perform the adjustment of these parameters since there is a possibility that the image quality of the reconstructed image greatly deteriorates depending on the setting of values.

Thus, the image quality of the reconstructed image is adjusted as the user adjusts the correction process in the newly added step ST1001 according to the present embodiment. An adjusting method according to the correction process ST1001 will be described.

First, an arbitrary correction process G2 shown in Formula (10) is performed with respect to an estimation result corrected in step ST404 in step ST1001.

[Formula 10]

$$\tilde{u}^{k+1} = G_2 \tilde{u}^{k+1} \qquad (10)$$

It is possible for the user to select, change and adjust processing content and a parameter of a correction process G2 using a keyboard, a mouse or the like serving as the input unit 119 of FIG. 1. An arbitrary correction process may be performed as the correction process G2 and, for example, a smoothing process such as Gaussian filter processing is performed when it is desired to further sharpen the reconstructed image. On the contrary, a sharpening process such as unsharp masking may be performed when it is desired to further suppress the noise.

In this case, a size, a variation or the like of the Gaussian filter, for example, is considered as the parameter input by the user. In addition, several sets of parameters may be prepared in advance and selected.

Figure 11:
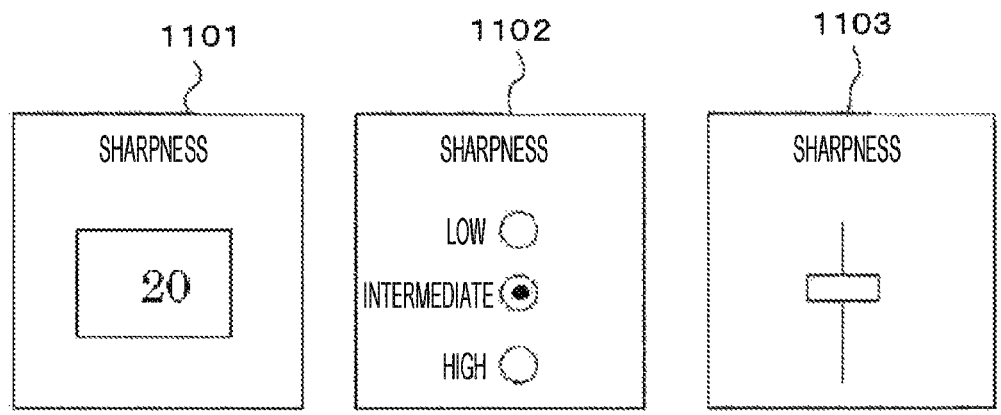
FIG. 11 is a diagram illustrating an example of a screen to be displayed to a user according to Embodiment 3.

FIG. 11 is an example of an adjustment screen to be displayed to the user using the display or the like serving as output unit 120 of the FIG. 1. For example, it is possible to adjust an item such as sharpness using a numeric value 1101, a check button 1102, a slider 1103, or the like.

In step ST1002 of FIG. 10, $f^{k+1}$ is updated using Formula (11).

[Formula 11]

$$f^{k+1} = f^k + f - \Phi \tilde{u}^{k+1} \qquad (11)$$

As above, it is possible to more simply adjust the image quality of the reconstructed image, and to significantly reduce the image quality adjusting work of the user according to the present embodiment.

Embodiment 4

Embodiment 4 is an embodiment of a case in which an image capturing apparatus is an ultrasonic diagnostic apparatus which is capable of acquiring a high-quality ultrasonic image at high speed.

Figure 12:
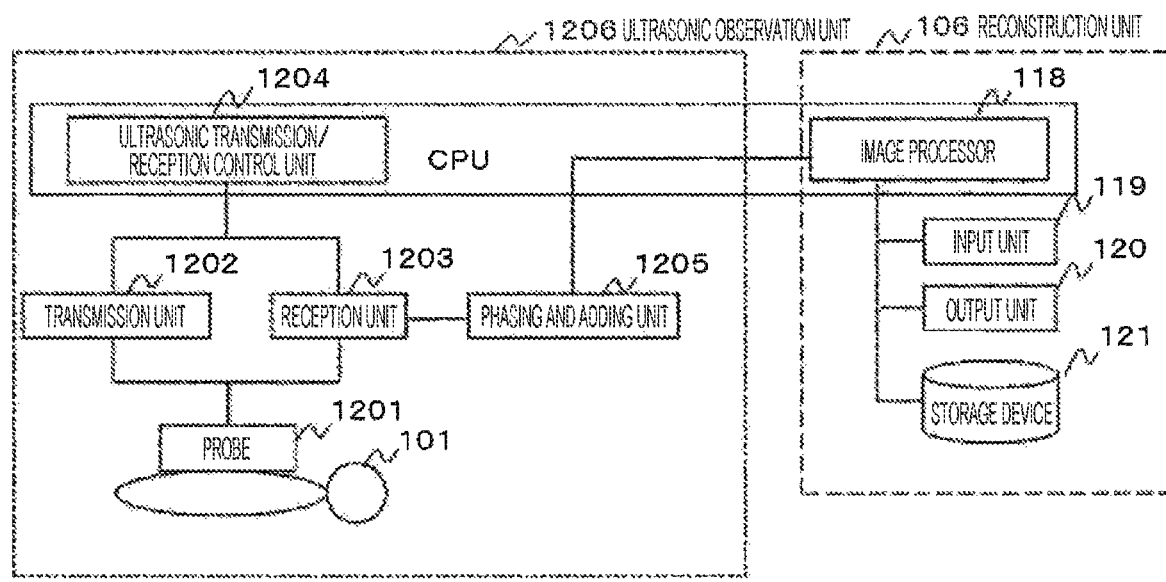
FIG. 12 is a block diagram illustrating an example of the entire configuration of an ultrasonic diagnostic apparatus according to Embodiment 4.

FIG. 12 is a block diagram illustrating a configuration example of the ultrasonic diagnostic apparatus as the image capturing apparatus according to Embodiment 4. In FIG. 12, the same elements as the constituent elements illustrated in FIG. 1 will be denoted by the same reference signs, and the description thereof will be omitted. In the same drawing, an ultrasonic observation unit 1206 forming the ultrasonic diagnostic apparatus is configured of an ultrasonic probe 1201, a transmission unit 1202, a reception unit 1203, an ultrasonic transmission/reception control unit 1204, and a phasing and adding unit 1205.

The transmission unit 1202 repeatedly transmits an ultrasonic wave to the subject 101 via the ultrasonic probe 1201 with a time interval. The reception unit 1203 receives time-series reflection echo signals generated from the subject 101. The ultrasonic transmission/reception control unit 1204 controls the transmission unit 1202 and the reception unit 1203. The phasing and adding unit 1205 phases and adds the received reflection echo signals, and generates RF signal frame data in a time-series manner. The phasing and adding unit 1205 includes a built-in analog/digital (A/D) converter, outputs the RF signal frame data to the image processor 118 of the reconstruction unit 106 as observation data, and the image processor 118 generates an ultrasonic echo image using the observation data including the RF signal frame data.

The ultrasonic observation unit 1206 of the present embodiment transmits a result of sparse observation to the image processor 118 as the observation data. Herein, examples of the sparse observation include thinning out transmission intervals of ultrasonic waves of the transmission unit 1202 and the like. The image processor 118 performs the reconstruction process illustrated in Embodiment 1 or Embodiment 3 with respect to the sparse observation result. Incidentally, the observed reflection echo signal is an image signal in the present embodiment, and thus, the same image processing as described in Embodiment 1 is performed without executing the above Fourier transform of Formula (1).

According to the ultrasonic diagnostic apparatus of the present embodiment, it is possible to acquire the high-quality ultrasonic image at the high speed.

Embodiment 5

Embodiment 5 is an embodiment of a case in which an image capturing apparatus is a CT apparatus which is capable of acquiring a high-quality CT (computed tomography) image at high speed.

Figure 13:
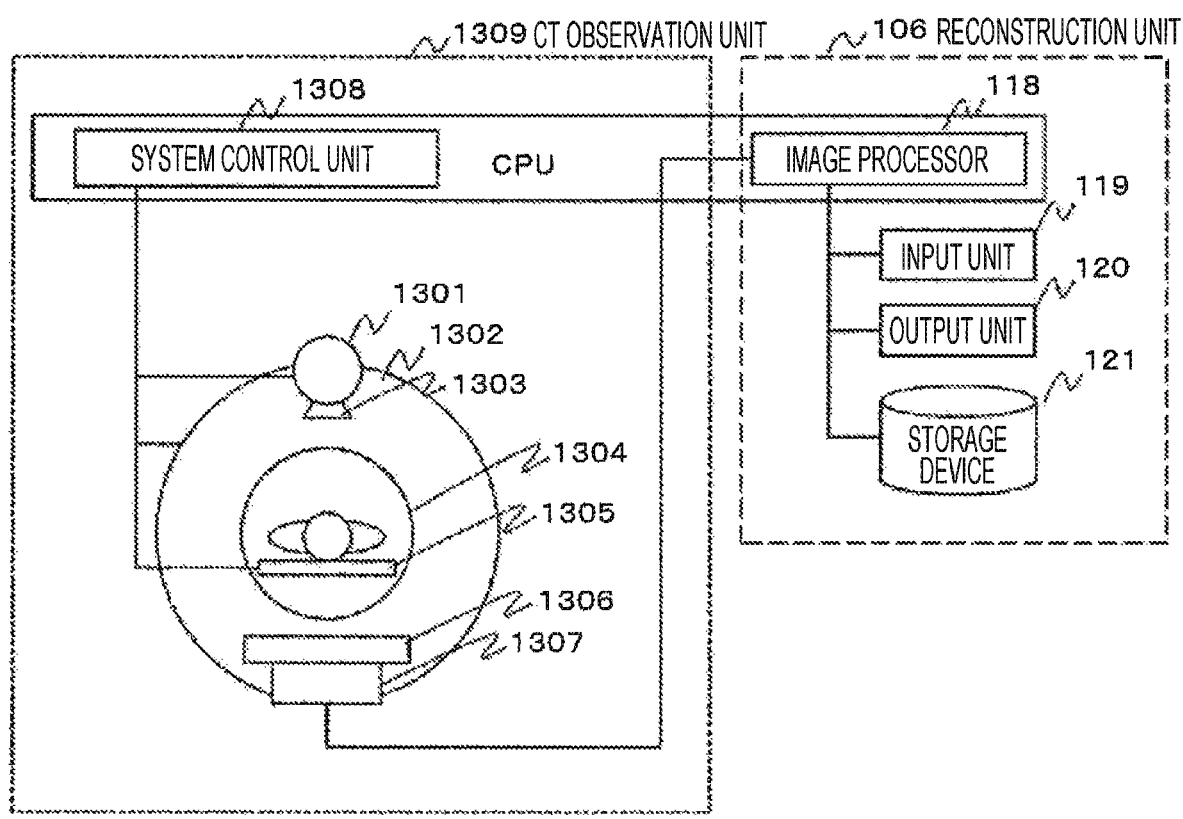
FIG. 13 is a block diagram illustrating an example of the entire configuration of a CT apparatus according to Embodiment 5.

FIG. 13 is a block diagram illustrating a configuration example of the CT (computed tomography) apparatus as the image capturing apparatus according to Embodiment 5. In the same drawing, the same elements as the constituent elements illustrated in FIGS. 1 and 12 will be denoted by the same reference signs, and the description thereof will be omitted.

In FIG. 13, a CT observation unit 1309 is configured of an X-ray tube apparatus 1301, a rotating disk 1302, a collimator 1303, an X-ray detector 1306, a data collection apparatus 1307, a couch 1305, and a system control unit 1308. The X-ray tube apparatus 1301 is an apparatus that irradiates a subject placed on the couch 1305 with an X-ray. The collimator 1303 is a device that restricts a radiation range of the X-ray emitted from the X-ray tube apparatus 1301. The rotating disk 1302 is provided with an opening portion 1304 which the subject placed on the couch 1305 enters, and is configured to rotate around the subject with the X-ray tube apparatus 1301 and the X-ray detector 1306 mounted thereto.

The X-ray detector 1306 is a device that is arranged to face the X-ray tube apparatus 1301, and measures the spatial distribution of transmission X-ray by detecting the X-ray that has transmitted through the subject, and is configured by arraying a large number of X-ray detection elements in a rotation direction of the rotating disk 1302 or two-dimensionally in the rotation direction and a rotation-axis direction of the rotating disk 1302. The data collection apparatus 1307 is a device that collects the amount of X-ray detected by the X-ray detector 1306 as digital data. In addition, the system control unit 1308 is configured to control the rotation of the rotating disk 1302, vertical, front-back, and horizontal movements of the couch 1305, power to be input to the X-ray tube apparatus 1301, and the like.

The CT observation unit 1309 of the CT apparatus of the present embodiment transmits the digital data, which is a result of sparse observation, to the image processor 118 of the reconstruction unit 106 as observation data. Herein, examples of the sparse observation include a case in which observation is not sufficiently performed with respect to angular directions at the time of performing the observation using the X-ray tube apparatus 1301 and the X-ray detector 1306, and the like. The image processor 118 of the reconstruction unit 106 of the present embodiment performs the reconstruction process illustrated in Embodiment 1 or Embodiment 3 with respect to the sparse observation result to reconstruct the high-quality CT image.

As above, it is possible to acquire the high-quality CT image at the high speed according to the present embodiment. Further, it is possible to expect reduction of the amount of exposure to the X-ray as compared to the related art.

Incidentally, the present invention is not limited to the above-described embodiments, and includes various modification examples. For example, the above-described embodiments have been described in detail in order to facilitate understanding of the present invention, and the invention is not necessarily limited to include the entire configuration described above. In addition, some configurations of a certain embodiment can be substituted by configurations of another embodiment, and further, a configuration of another embodiment can be added to a configuration of a certain embodiment. In addition, addition, deletion or substitution of other configurations can be made with respect to some configurations of each embodiment.

Further, the description has been given by exemplifying that a part or all of the configurations, functions and processing units may be realized by a program of the CPU, and apart or all of them may be realized by the hardware, for example, designed with an integrated circuit.

REFERENCE SIGNS LIST 100 observation unit
101 subject
102 static magnetic field generation system
103 gradient magnetic field generation system
104 transmission system
105 reception system
106 reconstruction unit
107 sequencer
108 central processing unit (CPU)
109 gradient magnetic field coil
110 gradient magnetic field power source
111 high frequency generator
112 modulator
113 amplifier
114 high frequency coil
115 amplifier
116 quadrature phase detector
117 A/D converter
118 image processor
119 input unit
120 output unit
121 storage apparatus
201 K-space
202 origin
203 low frequency region near origin
204 low frequency region near axis
205 high frequency region
301 horizontally-parallel-line form observation pattern
302 radial form observation pattern
303 random form observation pattern
501 true horizontal edge image
502 reconstructed horizontal edge image
601 moving average filter
602 Gaussian filter
701 smoothed observation pattern
801 observation point
802 observation point at position point-symmetric to observation point 801 with respect to origin 202
901 parallel-line form observation pattern
902 radial-line form observation pattern
903 random form observation pattern
1201 ultrasonic probe
1202 transmission unit
1203 reception unit
1204 ultrasonic transmission/reception control unit
1205 phasing and adding unit
1206 ultrasonic observation unit
1301 X-ray tube apparatus
1302 rotating disk
1303 collimator
1304 opening portion
1305 couch
1306 X-ray detector
1307 data collection apparatus
1308 system control unit
1309 CT observation unit

The invention claimed is:

1. An image capturing apparatus that images an image of a subject, the image capturing apparatus comprising:
   a magnetic resonance apparatus which performs sparse observation of the subject to collect data from the subject based on an observation pattern and outputs observation data; and
   an image processor which reconstructs an image from the observation data received from the magnetic resonance apparatus and iteratively performs an image correction process using a filter based on the observation pattern with respect to the observation data,
   wherein the image capturing apparatus is a magnetic resonance imaging apparatus, and the observation data is K-space data,
   the observation pattern of the magnetic resonance apparatus is a radial form on which observations are performed at angular directions that do not overlap each other even when being rotated by 180 degrees, and
   the image correction process of the image processor includes a smoothing process in which the observation pattern is smoothed by a Gaussian filter to form a smoothed observation pattern which is used as the filter in a next iteration of the image correction process.

2. The image capturing apparatus according to claim 1, wherein
   a result corrected by the image correction process is used in an estimation updating process thereof.

3. The image capturing apparatus according to claim 1, wherein
   when any one of two points which are point-symmetric with respect to an origin of the K-space is observed in a high frequency component of the K-space,
   the magnetic resonance apparatus does not perform observation for the other point.

4. The image capturing apparatus according to claim 1, wherein a plurality of image correction processes are performed by the image processor.

5. An image capturing apparatus that images an image of a subject, the image capturing apparatus comprising:

a magnetic resonance apparatus which performs sparse observation of the subject to collect data from the subject based on an observation pattern and outputs observation data of a K-space; and an image processor which reconstructs an image from the observation data from the magnetic resonance apparatus and iteratively performs an image correction process using a filter based on the observation pattern with respect to the observation data, wherein the magnetic resonance apparatus does not perform the sparse observation, when any one between two points which are point-symmetric with respect to an origin of the K-space is observed in a high frequency component of the K-space, for the other point, the observation pattern of the magnetic resonance apparatus is a radial form on which observations are performed at angular directions that do not overlap each other even when being rotated by 180 degrees, and the image correction process of the image processor includes a smoothing process in which the observation pattern is smoothed by a Gaussian filter to form a smoothed observation pattern which is used as the filter in a next iteration of the image correction process.

6. The image capturing apparatus according to claim 5, wherein the image processor performs an image correction process based on the observation pattern with respect to the observation data of the K-space.

7. The image capturing apparatus according to claim 6, wherein the image correction process performed by the image processor is repeated a plurality of times.

8. An image capturing method that images an image of a subject, the image capturing method comprising:

acquiring observation data of the subject based on an observation pattern to perform sparse observation; and iteratively performing an image correction process using a filter based on the observation pattern with respect to the observation data when an image is reconstructed from the observation data, wherein the observation data is data of a K-space which is acquired by an observation unit of an MM apparatus, the observation pattern is a radial form on which observations are performed at angular directions that do not overlap each other even when being rotated by 180 degrees, and the image correction process of the reconstruction unit includes a smoothing process in which the observation pattern is smoothed by a Gaussian filter to form a smoothed observation pattern which is used as the filter in a next iteration of the image correction process.

9. The image capturing method according to 8, wherein when any one of two points which are point-symmetric with respect to an origin of the K-space is observed in observation of a high frequency component of the K-space, observation for the other point is not performed.

* * * * *